United States Patent
Livingston et al.

(10) Patent No.: US 7,718,064 B2
(45) Date of Patent: May 18, 2010

(54) INTEGRATED CLEAN BIOMASS TO ENERGY SYSTEM

(75) Inventors: Kevin S. Livingston, Harrison Township, MI (US); Glenn T. Hummel, Royal Oak, MI (US)

(73) Assignee: Hesco Sustainable Energy, LLC, Warren, MI (US)

(*) Notice: Subject to any disclaimer, the term of this patent is extended or adjusted under 35 U.S.C. 154(b) by 0 days.

(21) Appl. No.: 11/675,175

(22) Filed: Feb. 15, 2007

(65) Prior Publication Data
US 2007/0193948 A1    Aug. 23, 2007

Related U.S. Application Data

(60) Provisional application No. 60/774,774, filed on Feb. 17, 2006.

(51) Int. Cl.
    C02F 11/04    (2006.01)
    C02F 3/28     (2006.01)
(52) U.S. Cl. .................. 210/603; 210/609; 210/613
(58) Field of Classification Search .......... 210/603, 210/609, 612, 613
    See application file for complete search history.

(56) References Cited

U.S. PATENT DOCUMENTS

| | | | | |
|---|---|---|---|---|
| 5,746,919 A | * | 5/1998 | Dague et al. ........... | 210/603 |
| 6,405,664 B1 | * | 6/2002 | Logan et al. ........... | 110/345 |
| 6,613,562 B2 | * | 9/2003 | Dvorak ................ | 435/290.4 |
| 6,632,362 B2 | * | 10/2003 | Miller, III ........... | 210/603 |
| 2001/0023853 A1 | * | 9/2001 | Millard et al. ........ | 210/764 |
| 2002/0079266 A1 | * | 6/2002 | Ainsworth et al. ..... | 210/603 |
| 2002/0148778 A1 | * | 10/2002 | Raven ................ | 210/603 |
| 2004/0011718 A1 | * | 1/2004 | Arnett et al. ........ | 210/175 |
| 2004/0164019 A1 | * | 8/2004 | Fassbender ........... | 210/603 |

FOREIGN PATENT DOCUMENTS

JP    2002-066246    * 3/2002

OTHER PUBLICATIONS

Bivins et al., Nov. 4, 2003, Biosolids Group, Bulletin No. 1: 1-5.

* cited by examiner

*Primary Examiner*—Fred Prince
(74) *Attorney, Agent, or Firm*—McDonnell Boehnen Hulbert & Berghoff LLP; Michelle McMullen-Tack

(57) ABSTRACT

The invention provides improved methods of wastewater purification. The present invention provides a process for the energy efficient production of Class A biosolids. More particularly, sewage sludge is subjected to an anaerobic digestion process resulting in class A biosolids, whereby methane gas byproducts are utilized to meet the high energy demands associated with Class A biosolid production.

17 Claims, 1 Drawing Sheet

INTEGRATED CLEAN BIOMASS TO ENERGY SYSTEM

This application claims priority to U.S. Provisional Application Ser. No. 60/774,774, filed Feb. 17, 2006, which is explicitly incorporated by reference herein.

FIELD OF THE INVENTION

This invention relates generally to the art and science of wastewater treatment. In particular, this invention relates to a method for the economical production of Class A biosolids via the utilization of methane byproducts as a renewable power source. The invention provides an energy efficient and environmentally safe wastewater treatment process, and thus is an improvement over prior wastewater treatment methods.

BACKGROUND OF THE INVENTION

A typical wastewater treatment facility accepts input wastewater containing solid and dissolved waste matter. The solids and dissolved matter are removed, and the water is purified prior to discharge into the environment. The waste solids are commonly referred to as sludge or biosolids. Biosolids contain viral and bacterial pathogens, organic and inorganic contaminates. Thus biosolids pose a safety and health risk to humans and the environment. Biosolids have historically been disposed of by incineration, landfilling, or land application. Generally over half of wastewater facilities' operating costs are associated with the handling and disposal of biosolids.

An alternative to landfill disposal and/or incineration is the production of environmentally safe biosolids, including Class A biosolids. Biosolids purified to United States Environmental Protection Agency's (EPA's) Class A standards result in the virtual elimination of pathogens. Class A biosolids are safe enough to be utilized as fertilizer on agricultural land and possess almost no application restrictions.

Although meeting Class A standards permits the recycling of biosolids and eliminates costs associated with incineration or transfer to landfill, conventional processes for producing Class A pathogen levels are very costly. Class A biosolids require a significant amount of energy to process, and are thus associated with extremely high fuel demands. There exists an economic disincentive for Class A biosolid production, which in turn has hampered its widespread adoption.

Anaerobic digestion has been one of the most widely used processes for the stabilization of primary and secondary sludges produced at municipal wastewater treatment facilities, but the majority of applications of anaerobic digestion to wastewater sludges have been in the mesophilic temperature range, from 35° C. to 40° C. (95° F. to 104° F.). Anaerobic sludge digestion in the thermophilic temperature range, necessary for producing Class A biosolids, is performed at 45° C. to 65° C. (113° F. to 149° F.) but has been practiced to only a limited extent. The limited use of anaerobic digestion at higher thermophilic temperatures is due to the greatly increased energy demands and high fuel (e.g., natural gas) costs.

The advantages of thermophilic digestion include increased stabilization and methane production rates, and improved sludge dewatering properties. Furthermore, thermophillic anaerobic digestion coupled with a mesophilic digestion has improved pathogen destruction and meets the pathogen quality requirements for EPA's Class A biosolid certification. However, there exists a need for cost-efficient Class A biosolid processing.

Anaerobic digestion processes produce biogas byproducts such as $CO_2$, nitrogen, and methane. Generally, this renewable source of energy is flared as a gas byproduct. Advantageously, the significant amounts of methane should be converted to usable heat and electricity. There exists a need for a cost-efficient method for harnessing the energy potential inherent in wastewater treatment process and utilizing said energy to sustain the wastewater treatment process.

SUMMARY OF THE INVENTION

Accordingly, it is a general object of the invention to overcome the deficiencies in the wastewater treatment art, particularly directed to more energy-efficient Class A biosolid production. The present invention advantageously provides methods for reducing the high energy costs associated with Class A biosolid production by utilizing methane byproducts as a renewable energy supply.

In one aspect, the invention provides methods for reducing external energy requirements/costs associated with the production of Class A biosolids. In advantageous embodiments, this invention provides methods for optimizing energy requirements associated with biosolid processing and detoxification by coupling the energy demands of Class A biosolid sludge treatment with the energy yield obtained from the conversion of methane byproducts into useable energy.

The present invention also provides methods for capturing the energy available from methane byproducts and using said energy to reduce the costs associated with the production of Class A biosolids. Certain embodiments of the methods of this invention comprise large-scale production of anaerobic Class A biosolids economically by using co-produced methane to reduce reliance on external energy sources.

The method of the invention provides a renewable energy supply for the economically efficient and environmentally safe conversion of sludge to Class A biosolids. A further aspect of the invention is large-scale production of Class A biosolids as a means of reducing costs/external energy requirements associated with the disposal of pathogenic biosolids.

The invention provides methods for converting sewage sludge to electricity having improved efficiency over conventional methods. Biogases including methane produced during sewage detoxification are collected and cleansed of impurities. After cleansing, the gas is used as fuel for electrical generation equipment such as natural gas generators or gas micro turbines. These machines generate electricity that can be utilized to meet the energy requirements for equipment used in the wastewater treatment process.

These and other aspects of this invention are, in certain embodiments, implemented by generating electricity in which the sewage sludge is first digested in an anaerobic digester, thereby forming a gas mixture of methane and carbon dioxide. Multi-stage anaerobic bio-digesters may be employed for this purpose. Water present in the digested sludge is then removed, forming dewatered sludge. The water may be removed by any number of known methods, such as clarification, gravity thickening, filtration, centrifugation, and thermal drying.

In additional aspects, the invention provides methods for utilizing waste heat in the treatment process. The machines used in the wastewater treatment process generate waste heat. This heat may be collected and used to meet the heating demands of the thermophilic phase of the treatment process, and/or drying of the digested sludge. Furthermore, heat and electricity generated in excess of that used in the anaerobic digestion process can be used as a power source to meet other energy requirements of the plant. Furthermore, waste heat and electricity from the generation step may be used to dry the Class A biosolids to the appropriate level.

These and other additional aspects and advantages are achieved in a unique combination of methods and systems for treating sludge generated in a wastewater treatment facility according to the present invention.

Specific preferred embodiments of the present invention will become evident from the following more detailed description of certain preferred embodiments and the claims.

DESCRIPTION OF THE DRAWINGS

These and other objects and features of this invention will be better understood from the following detailed description taken in conjunction with the drawing wherein.

DETAILED DESCRIPTION OF THE PREFERRED EMBODIMENTS

Figure 1:
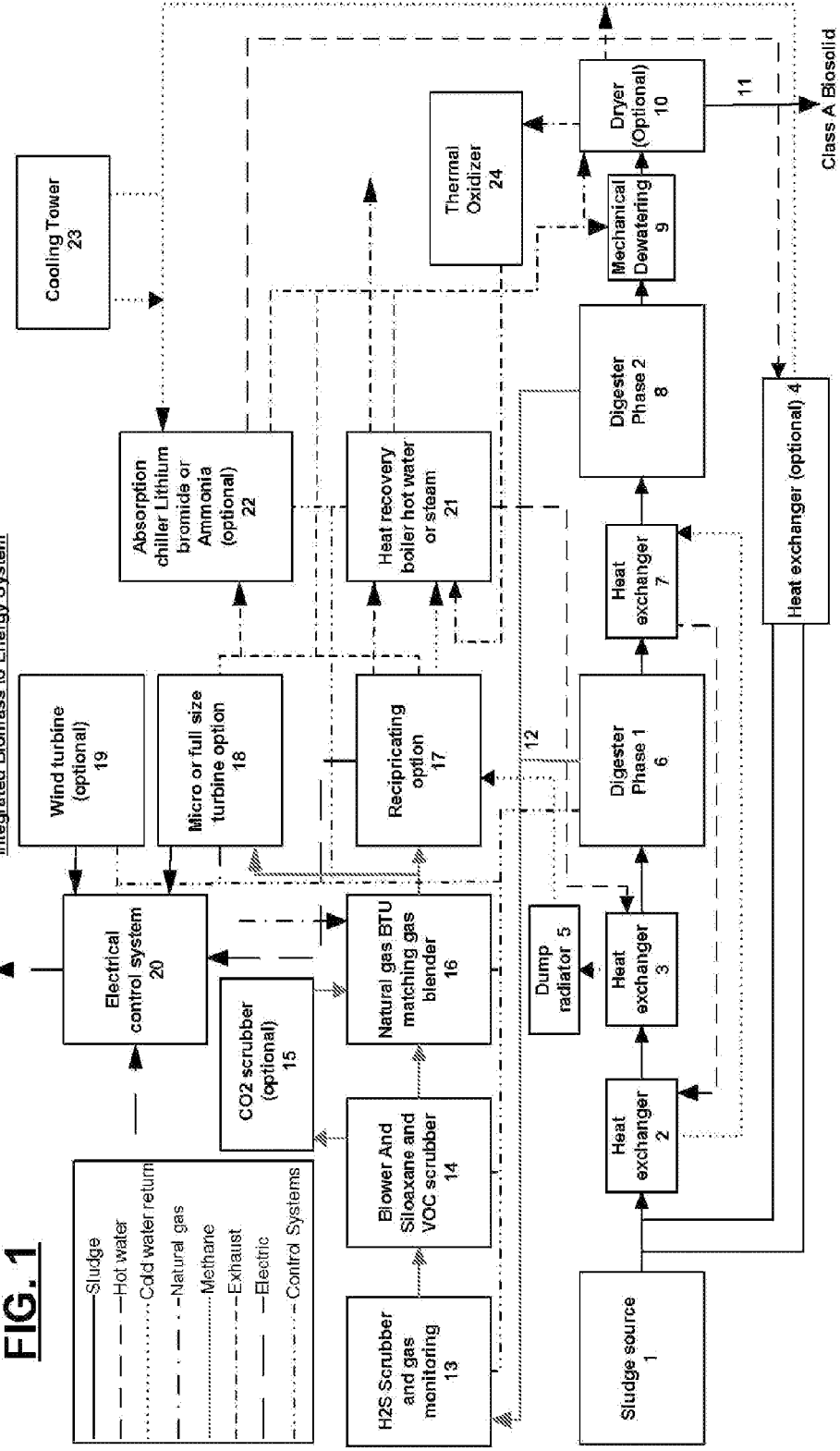
FIG. 1 is a schematic diagram representation of an integrated biomass to energy wastewater treatment process according to one embodiment of the present invention.

The present invention provides methods for improving energy efficiency in wastewater treatment by integrating energy consumed by the anaerobic digestion of wastewater sludge into Class A biosolids with the energy yielded from such treatment in the form of methane gas emissions. The resulting methane gas may preferably be converted into energy to self-sustain operation of anaerobic digestion into Class A biosolids, energy not consumed by the digestion process may be utilized to supply energy to other aspects in the wastewater treatment facility.

In the description that follows, it is assumed that raw wastewater flowing into a wastewater treatment plant has undergone the following conventional treatment steps: screening, primary sedimentation, secondary sedimentation, trickle filter treatment and/or activated sludge treatment. The sludges collected from the various stages have been thickened to an appropriate solids content.

The term "wastewater sludge" as used herein refers to sludge comprised of the solids portion of the inflow of a wastewater treatment plant. Said sludge is often unprocessed and is referred to as raw sludge. Wastewater sludge includes waste activated sludge (WAS) and primary sludge (PS) or a mixture of both. Wastewater sludge may also include microorganisms, organic materials and inorganic precipitates. Wastewater sludge may be derived from but not limited to the following sludges: pharmaceutical production sludge, bacterial fermentation sludge, sludge from alcoholic beverage production, paper mill sludge, rendering plant sludge and livestock feedlot sludges.

Incoming wastewater is subjected to screening and initial sedimentation steps that are conventionally performed at a wastewater treatment facility. Resulting sludge, which may contain, for example, between 94-97% water by weight (4-6% dry solids), is subjected to anaerobic digestion to produce Class A biosolids and a biogas mixture.

The term "treated wastewater sludge" as used herein refers to sludge that has been subjected to some form of wastewater treatment processing and includes but is not limited to screening, anaerobic digestion, or sedimentation.

The biogas mixture may contain methane in a range of about 55-75% percent by weight of the carbonaceous solids present in the sludge when converted to gas, leaving behind a residue of digested sludge meeting Class A certification standards. Anaerobic digestion may be accomplished by any of the several methods known in the art, including single phase, two-phase, or multi-phase digestion. In addition, two-phase or multi-phase digestion may occur in a single tank or in separate tanks In a preferred embodiment, two-stage anaerobic digestion is practiced by the methods of the invention. Anaerobic digestion preferably includes a thermophilic digestion (acid phase) at approximately 55° C. for about 2 days and a mesophilic digestion (gas phase) at approximately 37° C. for about 10 days. In a preferred embodiment, the two-phases of anaerobic digestion occur in separate digester tanks. In an additional embodiment, the digestion may include a lysis technique to improve digestion rates.

The invention disclosed herein is a multi-step method for achieving improved utility from sewage sludge. The method of the invention is a process to reduce pathogen densities in sludge to meet Class A certification as defined in Title 40, Consolidated Federal Rules (C.F.R.), Part 503, and to meet expected standards as may be defined by the Environmental Protection Agency Pathogenic Equivalency Committee (PEC).

EPA has determined two levels of treatment, Class A and Class B, which are acceptable for the disposal of biosolids as agricultural fertilizer. Class B is simpler to attain, but has several restrictions on its use and application. Class A has virtually no application restrictions. Unfortunately, Class A treatment processes fail to be cost effective because they consume greater amounts of energy than traditional sludge stabilization and treatment methods.

The term "Class A biosolid(s)" as used herein refers to sewage sludge that has met the requirements of 40 C.F.R. § 503.32. In general, EPA Class A pathogen requirements are met in biosolids when fecal coliform densities are less than 1,000 Most Probable Number (MPN) per gram total solids (dry weight density); or when Salmonella densities are less than 3 MPN per four grams total solids at the time the sewage sludge is used or disposed; at the time the sewage sludge is prepared for sale or give away in a bag or other container for application to the land; or at the time the sewage sludge or material derived from sewage sludge is prepared to meet the requirements of the various alternatives under § 503.32. Enteric virus density must be less than one plaque-forming unit (pfu) per four grams of total solids (dry weight basis) and helminth ova is less than one viable helminth ova per four grams of total solids. Additionally, the EPA provides time and temperature requirements under 40 CFR § 503.32(a) (3)-Alternative 1, that state the required reduction in pathogen densities. 40 CFR § 503.32 is herein incorporated by reference as the standard for Class A biosolids.

The term "Class A biosolid processing" as used herein refers to wastewater treatment purification beginning with wastewater inflow into a treatment plant and ending with sludge or biosolids meeting the EPA's Class A certification standards.

The term "disposing" as used herein refers but is not limited to removal from the wastewater treatment facility, landfill disposal, incineration, preparation of the Class A biosolids for sale or give away in a bag or other container for application to the land or other uses.

Following anaerobic digestion, the sludge is dewatered by any suitable means known to those skilled in the art, including the use of a centrifuge, filter press, or filter, or the use of a dryer, or the use of a combination of these methods. After removal of the water from the digested sludge, the solids content in the remainder of the sludge may increase to a range of 25-50 percent by weight of the sludge in the case of mechanical dewatering or greater than 90% in the case of thermal drying. The water content of the final product would be determined by the end users' product requirements and could vary by geography. In a preferred embodiment, the resulting biosolid meets Class A certification.

Heat is employed for drying the residual sludge from the digesters. In a preferred embodiment, waste heat resulting from the electrical generation equipment is collected and utilized for the drying process. Furthermore, electricity produced from methane byproducts can be used to power the drying process.

The phrase "meet the heating requirements" and the term "heat" as used herein refers to the satisfaction of a portion or all of the heating demands for sludge dehydration. In a preferred embodiment, the invention reduces the use of external energy sources for sludge drying by using heat generated in the process or using biogas produced thereby to generate heat. Reducing dependency on external energy sources regardless of the percentage of reduction is sufficient.

With anaerobic digestion, one of the byproducts of the digestion process is methane gas. The methane gas can be recovered and converted to energy, particularly electrical energy or heat energy. Recovered methane is associated with other biogases and contaminates such as $CO_2$, nitrogen, $H_2S$ and siloxanes. Some impurities damage power generation equipment, while others have foul odors. Advantageously, therefore, the methane gas is cleaned according to methods known in the art prior to combustion.

The methane gas produced by anaerobic digestion methods can be used as a renewable fuel source for electrical generation equipment such as natural gas generators or gas micro turbines. These machines generate electricity that can be utilized in the meet the energy requirements for equipment used in the wastewater treatment process. The energy obtained from methane emissions can be used to meet the high energy demands of Class A anaerobic digestion.

The phrase "meet energy requirements associated with Class A biosolid processing" as used herein may include the satisfaction of a portion or all of the input energy requirements of a wastewater treatment facility. In a preferred embodiment, the present invention produces energy equivalent to the input energy requirement of anaerobic digestion. In an alternative embodiment, "meet the energy requirements associated with Class A biosolid processing" may encompass the satisfaction of some or all of the general energy requirements associated with other aspects of processing, such as sludge drying. Reducing dependency on external energy sources, such as natural gas, for example, is sufficient regardless of the percentage of reduction.

The anaerobic digesters can be expected to recover bio-gas in the range of 12-17 cubic feet/pound of VSS destroyed in digestion. Methane generation may vary according to the percentage of volatile suspended solids (VSS) in the digested sludge as will be understood by those of skill in the art. Additional energy derived from methane conversion may be used to power other parts of the wastewater treatment facility, such as the drying process.

FIG. 1 is a schematic diagram of an integrated biomass to energy system that may be used by a wastewater treatment facility. The schematic is merely an example and provides one embodiment of the present invention. Inflowing wastewater is subjected to conventional treatment typically employing an aerobic treatment process that is known in the art. Primary and Secondary sludge is collected for production of the sludge source 1. The collected sludge is heated as it passes through heat exchangers 2, 3 and into a first digestion tank 6. Here the sludge is subjected to the first phase of anaerobic digestion at the appropriate temperature range and duration as required for the production of Class A biosolids. Next, the treated sludge is cooled as it passes through another heat exchanger 7 and into a second digester tank 8. The sludge is subjected to a second phase of anaerobic digestion at the appropriate temperature and duration. Following digestion, the treated sludge is dewatered and dried according to known methods, such as mechanical dewatering 9 or thermal drying 10. The resulting Class A biosolids can be recycled as fertilizer or utilized in other applications 11.

Methane gas released during anaerobic digestion is collected 12 and subjected to purification via a series of scrubbers including: a $H_2S$ scrubber 13, siloxane and VOC scrubber 14, and an optional $CO_2$ scrubber 15. Cleansed methane is then converted into usable energy to self-sustain the digester operations 6 and 8 as well as supply energy to other aspects of the treatment system. The methane may be combined with natural gas if necessary 16 prior to being converted to electricity via a reciprocating option 17 or a turbine 18. Additionally, other energy inputs may be utilized such as an optional wind turbine 19. Input electricity is sent to an electrical control system 20, which coordinates and manages the electrical requirements of the various subsystems, including the anaerobic digesters 6 and 8. Excess heat is recovered 21, 22, and used to aid in the drying and provide heat to the heat exchangers: 2, 3, 4, and 8.

A series of steps have been summarized for integrated energy consumption and energy production accorded to the invention. Steps may be added, removed, or modified without departing from the scope of the invention. Thus the invention is not intended to be limited to the disclosed embodiments of the invention. It should be understood that the foregoing disclosure emphasizes certain specific embodiments of the invention and that all modifications or alternatives equivalent thereto are within the spirit and scope of the invention as set forth in the appended claims.

The invention claimed is:

1. A method for treatment of wastewater sludge comprising:
    anaerobic digestion of wastewater sludge;
    disposing of said treated wastewater sludge as a Class A biosolid;
    capturing methane gas released during anaerobic digestion;
    converting said methane gas into an energy source, wherein the energy source includes electrical energy;
    utilizing said energy source to meet substantially all energy requirements associated with Class A biosolid processing;
    capturing heat from machinery emissions, wherein captured heat is used to dry the treated wastewater sludge as a Class A biosolid; and
    utilizing said heat to meet substantially all the heating requirements associated with Class A biosolid processing.

2. A method for integrated energy consumption and energy production for the treatment of wastewater sludge comprising:
    anaerobic digestion at thermophilic conditions;
    anaerobic digestion at mesophilic conditions permitting the release of methane gas;
    disposing of the treated wastewater sludge as a Class A biosolid;
    capturing and converting the methane gas to an energy source;
    utilizing said energy source to meet substantially all the energy requirements associated with Class A biosolid processing;

capturing heat from machinery emissions, wherein captured heat is used to dry the treated wastewater sludge as a Class A biosolid; and utilizing said heat to meet substantially all the heating requirements associated with Class A biosolid processing.

3. The method of claim 1 or claim 2, wherein the anaerobic digestion is performed in a plurality of tanks.

4. The method of claim 2, wherein the thermophilic condition is in a temperature range of between about 45° C. to about 59° C.

5. The method of claim 2, wherein the thermophilic condition is at a temperature of about 55° C.

6. The method of claim 4 or claim 5, wherein the anaerobic digestion at a thermophilic temperature is about 2 days.

7. The method of claim 2, wherein the mesophilic condition is in a temperature range of between about 35° C. to 40° C.

8. The method of claim 2, wherein the mesophilic condition is at a temperature of about 37° C.

9. The method of claim 7 or claim 8, wherein the anaerobic digestion at a mesophilic temperature is about 10 days.

10. The method of claim 1 or claim 2, wherein converting said methane to an energy source further comprises:

removing contaminates associated with said methane; and combusting purified methane to produce electricity.

11. The method of claim 10, wherein contaminates are siloxanes or $H_2S$.

12. The method of claim 10, wherein the electricity is used to meet substantially all of the input energy requirements associated with anaerobic digestion.

13. The method of claim 10, wherein the electricity is used to meet substantially all of the input energy requirements of a wastewater treatment plant.

14. The method of claim 1 or claim 2, wherein heat from machinery emissions comprises heat from generators.

15. The method of claim 1 or claim 2, wherein the volume of biosolids is reduced by a percentage greater than or equal to 36%.

16. The method of claim 1 or claim 2, wherein the volume of methane gas released during anaerobic digestion is greater than or equal to 12-17 cubic feet per pound of VSS destroyed.

17. The method of claim 1 or claim 2, wherein an integrated process control and electrical distribution system are utilized to orchestrate the energy requirements of the various steps in Class A biosolid processing.

* * * * *